United States Patent
Kostansek et al.

(10) Patent No.: US 6,541,426 B1
(45) Date of Patent: Apr. 1, 2003

(54) METHOD TO PRODUCE PESTICIDE SUSPENSION CONCENTRATES

(75) Inventors: Edward Charles Kostansek, Buckingham, PA (US); William Dean Mathis, Doylestown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 180 days.

(21) Appl. No.: 09/583,494

(22) Filed: May 31, 2000

Related U.S. Application Data

(60) Provisional application No. 60/139,838, filed on Jun. 18, 1999.

(51) Int. Cl.$^7$ .............................. A01N 25/34; B01J 8/00
(52) U.S. Cl. ...................... 504/341; 504/352; 504/363; 514/937; 424/405; 23/293 R; 23/295 R
(58) Field of Search ................................. 504/341, 352, 504/363; 424/405; 514/937; 23/293 R, 295 R

(56) References Cited

U.S. PATENT DOCUMENTS

| | | | |
|---|---|---|---|
| 4,571,088 A | * 2/1986 | Frensch et al. ............. | 366/166 |
| 4,875,929 A | 10/1989 | Morgan et al. ................ | 71/121 |
| 5,147,412 A | * 9/1992 | Klinksiek et al. ......... | 23/293 R |
| 5,283,231 A | 2/1994 | Morgan et al. ............. | 504/148 |
| 5,290,751 A | * 3/1994 | Fiard et al. .................. | 504/116 |
| 5,317,004 A | * 5/1994 | Misselbrook et al. ....... | 504/116 |
| 5,539,021 A | 7/1996 | Pate et al. ................... | 523/335 |
| 5,599,768 A | 2/1997 | Hermansky ................. | 504/116 |
| 5,624,884 A | 4/1997 | Morgan et al. ............. | 504/148 |
| 5,679,619 A | 10/1997 | Morgan et al. ............. | 504/130 |

FOREIGN PATENT DOCUMENTS

| | | |
|---|---|---|
| EP | 0283247 B1 | 4/1993 |
| GB | 1 518 568 | 7/1978 |

* cited by examiner

*Primary Examiner*—S. Mark Clardy
(74) *Attorney, Agent, or Firm*—Thomas D. Rogerson

(57) ABSTRACT

The present invention relates to a method to produce suspension concentrates of pesticides, pharmaceuticals, biocides, and similar materials, using a melt emulsification process. The method is particularly applicable to pesticides which have a low water solubility. The particle size can be controlled to give particles from less than 5 microns ($\mu$) to less than 1$\mu$.

10 Claims, No Drawings

METHOD TO PRODUCE PESTICIDE SUSPENSION CONCENTRATES

This application claims the benefit of Provisional Application No. 60/139,838, filed Jun. 18, 1999.

The present invention relates to a method to produce suspension concentrates of pesticides, pharmaceuticals, biocides, and similar materials, using a melt emulsification process. The method is particularly applicable to pesticides which have a low water solubility. The particle size of the material in the concentrate can be controlled to give particles less than 5 microns ($\mu$), preferably less than 1$\mu$.

The efficacy of pesticides is often related to the size of the pesticide particle. Typically, the smaller the particle the greater the efficacy due to factors such as increased release rate and wider and more uniform coverage upon application. For this reason, there is a need to prepare pesticide formulations in which the pesticide has a small particle size, preferably less than 5$\mu$. Small particles are typically prepared by milling larger particles using any one or more conventional milling techniques such as, for example, air milling, hammer milling, crushing (jaw, gyratory cone, roller, impact), impact milling (stationary plates), tumble milling with grinding media (balls, rods), roller milling (feeding through a small gap), pin milling, jet air milling (spiral, opposed, fluidized). Unfortunately, pesticides which melt at temperatures below about 120° C. are often difficult to mill to small particle size using conventional milling techniques. This is because the extended milling times needed to reach such small size often heats up the pesticide. This, in turn, leads to particle agglomeration and/or fouling of the milling apparatus due to melting of the pesticide. To avoid such problems the milling apparatus often requires cryogenic or refrigerated cooling.

Small particle size formulations of pesticides which are amorphous materials may be prepared by melting the pesticide and then emulsifying it in an aqueous medium. However, for pesticides which are crystalline, it is very difficult to achieve a stable crystalline product by this route and at the same time maintain pesticide particle size in the micron to sub-micron range because of heat of crystallization and unfavorable crystallization kinetics.

British Patent 1 518 568 describes both batch and continuous methods of suspension production using a melt emulsification technique wherein melted pesticide is introduced slowly, with vigorous stirring, into an aqueous phase kept at a uniform temperature. The described process results in particles which vary in size from 1 to 100$\mu$, with a considerable portion greater than 10$\mu$. U.S. Pat. No. 5,539,021 describes the preparation of high internal phase ratio emulsions and latexes using a high shear mixer to prepare small particle size latexes and emulsions. This method requires hydrophobic liquids which are emulsified at very high ratios in a water phase and subsequently diluted for further use. In the case of solid resins, the resin is first dissolved in a solvent, then emulsified, then the solvent is removed to get a solid. This method does not generally work well for highly crystalline solids because large crystals are frequently formed. Thus, there is still a need for a process which will allow production of suspension concentrates of low melting but crystalline materials with small particle size.

We have discovered specific conditions under which a continuous melt emulsification/crystallization method is used to form a suspension concentrate of a crystalline, preferably low melting, solid in which the final particle size is controlled even into the sub-micron size range. The method comprises the steps of:

a) combining a stream comprising melted solid with a stream comprising a solvent; wherein:
   1) the melting point of the solid is from 40 to 180° C.;
   2) the temperature of the stream comprising melted solid is 5° C. or more above the melting point of the solid;
   3) the solid has a solubility of less than 1%, by weight, in the solvent at 25° C.;
   4) one or both of the streams further comprises a surfactant or dispersant or both; and b) mixing the combined streams in a confined chamber under high shear conditions wherein the melted solid first emulsifies forming particles 5$\mu$ or less in size which then cool to below their melting point and solidify before the particles leave the chamber.

This method will produce a suspension concentrate formulation comprised of particles of the solid which are less than 5$\mu$, often less than 1$\mu$ in size in the solvent. The small particle size ensures that the biological activity of the solid approaches that of a solvent-based emulsifiable concentrate of the solid, but when water is used as the solvent stream, with the added benefit of eliminating organic solvents. Small particle size also ensures high suspensibility of the solid in the solution concentrate, typically greater than 90%. The particles comprising the resulting composition have a unique morphology as a result of the crystallization process that occurs during the emulsification/crystallization under high shear conditions. In practice, when each particle crystallizes it often, but not always, forms a single crystal which will reflect the basic crystal structure of the solid itself. For example, the particle shape of the product from Example 1 below is that of flat plates. This morphology is far different from what would be obtained through conventional milling processes wherein the solid is crushed.

The method of this invention may be applied to any solid with a melting point from 40 to 180° C. which is crystalline. The term "crystalline" means a material which when melted and then cooled to a temperature below its melting point rapidly crystallizes (solidifies) through a process of nucleation and accretion. Although particularly applicable to pesticides, the method is also applicable to pharmaceuticals, biocides, dyes, other organic chemicals, and mixtures thereof. Preferably the melting point of the solid is from 40 to 120° C., more preferably from 50 to 110° C., even more preferably from 60 to 100° C.

If the solubility of the solid in the solvent is more than 1%, by weight, the stability of the resulting suspension may be poor. Poor stability is usually caused by "Ostwald ripening", a process in which small crystals present in a suspension gradually dissolve while large crystals grow larger or form agglomerates. To avoid this problem, the solubility of the solid in the solvent must be less than 1%, by weight at 25° C.; preferably less than 0.5%; more preferably less than 0.1%.

Solvent composition is not critical. However, the solid must have a solubility in the solvent of less than 1%, by weight at 25° C. and be capable of being emulsified in the solvent. The solvent may be water or an organic solvent such as, for example; oils, alcohols, ethers, ketones, alkanes, cycloalkanes, aromatic compounds, pyridines and other aromatic nitrogen containing compounds, or mixtures thereof. Water is the most preferred solvent because of its ability to form an emulsion of the melted solid as well as a stable suspension concentrate.

When the solid is a pesticide, the solvent stream may contain a second pesticide which may be the same as but, preferably, different than the solid. The second pesticide should be compatible with the solid pesticide in terms of use rates and locus to be treated. Such pesticides may be selected from herbicides, insecticides, fungicides, acaricides, and the like. When the solvent is water, preferably the second pesticide is water soluble, most preferably, a water soluble salt. Examples of such pesticides include sodium acifluorfen, salts of glyphosate, and the like.

The stream comprising the melted solid may further comprise a solvent in which the solid is soluble. This may aid in transporting the solid to the confined chamber. However, care must be taken that the solvent does not interfere with the emulsification process that occurs in the chamber. Preferably no solvent is used in the melted solid stream.

Either the stream comprising the melted solid, the stream comprising the solvent, or both must contain one or more surfactants, dispersants, or both. Surfactants may be anionic, cationic, non-ionic, or mixtures thereof. Surfactants and dispersants commonly used in the art can be found in the John W. McCutcheon, Inc. publication *Detergents and Emulsifiers, Annual,* Allured Publishing Company, Ridgewood, New Jersey, U.S.A. When present in the stream comprising the melted solid, surfactants and/or dispersants may be present at up to 20%, by weight, of the stream; preferably from 2 to 15%; more preferably from 4 to 10%. When present in the stream comprising the solvent, surfactants and/or dispersants may be present at up to 16%, by weight, of the stream; preferably from 3 to 12%; more preferably from 6 to 10%.

The term "high shear conditions" refers to turbulent mixing conditions which are sufficient to emulsify the melted solid in the solvent by forming droplets of the desired particle size in the confined chamber. One skilled in the art will recognize that any one of a variety of apparatus may be used to accomplish such mixing including; for example, rotor/stator homogenizers, inline emulsifiers, static mixers, piston homogenizers, ultrasonic homogenizers, and high-speed jets or nozzles. In-line homogenizers operating at high (e.g. 24,000) revolutions per minute ("rpm") are preferred.

One critical aspect of the invention is the residence time of the combined solid/solvent in the confined chamber. It is important that both emulsification and crystallization occur under high-shear conditions. The residence time must be sufficiently long such that the melted solid is first emulsified to form small droplets of the desired particle size and then the droplets have sufficient time to crystallize before exiting the chamber. If the residence time is too short, the emulsified droplets emerge from the chamber as a supercooled liquid which later crystallizes, typically forming unacceptably large crystals. However, if the residence time is too long, the crystallized particles can agglomerate into, again, unacceptably large agglomerates. Residence time is calculated by dividing the volume of the chamber by the total flow rate of the melted solid and the solvent streams through the chamber. Under typical conditions the residence time will be 5 seconds or less; preferably from 0.05 to 2 seconds; more preferably 0.08 to 0.2 seconds. The optimum residence time will vary depending upon the chamber geometry, the high-shear mixer geometry, the relative and total flow rates of the solid and solvent streams, the temperatures of the streams and the chamber, the physical/chemical properties of the solid, and the type and properties of surfactants and/or dispersants used. The proper balance of each of these factors must be determined experimentally using the following criteria:

a) Surfactant—The surfactant used in the emulsification will depend on the solid that is chosen for study. The following factors influence surfactant choice: surfactant chemistry and structure; surfactant hydrophilic/lipophilic balance (HLB); and blending properties with other surfactants. The concentration of the surfactant should also be varied to establish minimum and maximum values.

b) Heating Temperature—Compare different heating temperatures for the specific solid which is above its melting point. Heating above the melting point helps to liquefy the active ingredient in the chosen media.

c) Homogenization—Vary the rate and length of homogenization, as well as chamber temperature for homogenization.

d) Quenching—Quenching (i.e. maintaining the temperature of the chamber below that of the solid and solvent streams) is very important because it allows for immediate stabilization of the sample and helps to control the particle size and growth. Quenching variables are: temperature; rate of quenching; agitation conditions during quenching including homogenization, stirring, or swirling; and addition of crystallization enhancers and/or inhibitors.

e) Storage—Suspension concentrate storage conditions should vary to test the stability and activity under certain conditions such as room and elevated temperature; freeze/thaw cycling, and shipping tests.

f) Solid Loading—The upper limit for the amount of solid or active ingredient that can be emulsified with the smallest amount of surfactant and other additives while retaining small particle size and activity should be determined.

g) Pressure—Preferably the process is conducted at atmospheric pressure (since the solvent stream is preferably water below its boiling point) using sealed reactors. However, the pressure may increase slightly if the temperature of either stream approaches or exceeds 95° C. Increasing the pressure will lower the melting temperature of solids and increase the boiling point of water which may enable the application to high melting solids in water media. Pressure may also have a similar effect on non-aqueous solvents, particularly those with boiling points near or below the melting point of the solid.

h) Emulsification Media—Emulsification media other than water can also be utilized including polar and non-polar solvents and oils, so long as the active ingredients have limited solubility in the chosen media.

The temperature of the solvent stream must be sufficiently below the melting point of the solid that the droplets of emulsified melted solid will crystallize before leaving the confined chamber. Preferably, the temperature of the solvent stream is from 20 to 110° C. below the melting point of the solid; more preferably from 40 to 105° C. below the melting point of the solid; most preferably from 60 to 100° C. below the melting point of the solid.

Preferably, the relative flow rates of the melted solid stream and the solvent stream are such that the amount of solid present in the mixture after exiting the chamber is 5 to 75% by weight; preferably 15 to 70%; more preferably 25 to 60%; most preferably 35 to 50%. This will result in a stable suspension concentrate.

The method results in a suspension concentrate in which the particlem size is less than $5\mu$, preferably less than $1\mu$, calculated as volume average particle size. Particle size is determined either optically, with a scanning electron microscope, or using commercial particle sizers, such as a Coulter LS™ particle sizer (Coulter Instruments).

It is often desirable to include in the suspension concentrate one or more adjuvants, such as additional surfactants and/or dispersants, wetting agents, spreading agents, dispersing agents, stickers, adhesives, defoamers, thickeners, emulsifying agents and the like. Such adjuvants commonly used in the art can be found in the John W. McCutcheon, Inc. publication *Detergents and Emulsifiers, Annual*, Allured Publishing Company, Ridgewood, N.J., U.S.A. One or more of such adjuvants may be added to either or both the melted solid stream or the solvent stream. Optionally, adjuvants may be added to the suspension concentrate itself.

Although the method of this invention produces stable solution concentrates, one or more post-treatment steps may be used to vary the properties of the final material. These include additional processing such as milling to reduce any agglomerates that may have formed or to further reduce the particle size of the solid; when the solid is a pesticide, addition of one or more additional pesticides or pesticide formulations, as noted earlier, preferably a water soluble pesticide; addition of adjuvants; extruding or drying the concentrate to obtain a solid material, and the like.

When the solid is a pesticide, typical practice of the method is as follows:

a) Dissolve appropriate surfactants and/or dispersants in a melted pesticide in a heated vessel;

b) Dissolve appropriate surfactants, dispersants, wetting agents, and/or glycols in water in a vessel having the option of being cooled or heated;

c) Pump the melted pesticide solution and the aqueous solution into a confined chamber in-line homogenizer operating under high-shear conditions;

d) Maintain the residence time in the homogenizer such that the pesticide melt emulsifies forming particles $5\mu$ or less in size which then cool below their melting point and solidify before exiting the homogenizer;

e) Mix in final formulation additives such as defoamer and thickener; and f) Optionally, post-treat the suspension concentrate.

The solution concentrates of pesticides prepared by the process of this invention can be diluted or applied as is to plant foliage or soil as aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the pesticide application rate, and the pests to be controlled. It may be desirable to include one or more additional adjuvants in the spray tank. The concentrates can also be mixed with fertilizers or fertilizing materials before their application. The concentrates can be utilized as the sole pesticidal agent or they can be employed in conjunction with other pesticidal agents such as, for example, microbicides, fungicides, herbicides, insecticides, acaricides, and the like.

The following examples illustrate several aspects of the method of this invention:

EXAMPLE 1

Oxyfluorfen

Eighty grams of oxyfluorfen herbicide (72% technical, melting point 75° C.) was melted with 6.4 g (8%, by weight, based on oxyfluorfen) of Sponto™ 234T surfactant (Witco Chemical Co.) in a 250 ml round bottom flask. The temperature was maintained at 105° C. The oxyfluorfen melt was pumped through heat-traced tubing and merged with a stream of water at 25° C. immediately before entering an in-line homogenizer (IKA Ultra Turrax™ homogenizer with a fine homogenizer tip) operating at 24,000 rpm. The flow rate of the oxyfluorfen stream was 15 ml/min. and the flow rate of the aqueous stream was 40 ml/min. The resulting suspension exiting the homogenizer was 28% solids and had the following particle size distribution as measured by laser light scattering on Coulter LS™ 130 particle sizer:

10%<$0.5\mu$ diameter

50%<$0.86\mu$

90%<$2.59\mu$

The particles were in the form of flat plates.

EXAMPLE 2

Propanil

Two hundred fifteen grams of propanil herbicide (melting point 90° C.) were melted with 8.0 g (3.7%, by weight, based on propanil) of Toximul™ 804 surfactant (Stepan Co.) in a 250 ml round bottom flask. The temperature of the melt was maintained at 102° C. The melt was pumped through heat-traced tubing and merged with an aqueous stream at −10° C. immediately before entering an in-line homogenizer (IKA Ultra Turrax™ homogenizer with a fine homogenizer tip) operating at 24,000 rpm. The aqueous stream consisted of 23.6% Soprophor™ FLK surfactant (Rhodia, Inc.) and 9.5% propylene glycol in water. The flow rate of the propanil stream was 150 ml/min. and the flow rate of the aqueous stream was 450 ml/min. The resulting suspension exiting the homogenizer was 29% solids and had an average particle size of $2\mu$ based on microscopic analysis of the non-spherical crystalline particles.

We claim:

1. A method to form a suspension concentrate of a crystalline solid with a particle size of 5 microns or less, comprising the steps of:

a) combining a stream comprising melted solid with a stream comprising a solvent; wherein:

1) the melting point of the solid is from 40 to 120° C.;
2) the temperature of the stream comprising melted solid is 5° C. or more above the melting point of the solid;
3) the solid has a solubility of less than 1%, by weight, in the solvent at 25° C.;
4) one or both of the streams further comprises a surfactant or dispersant or both; and b) mixing the combined streams in a confined chamber under high shear conditions wherein the melted solid first emulsifies forming particles 5$\mu$ or less in size which then cool to below their melting point and solidify before the particles leave the chamber and wherein the residence time of the combined solid and solvent streams in the confined chamber is 5 seconds or less.

2. The method of claim 1 wherein the solvent is water.

3. The method of claim 1 wherein the solid is a pesticide, a pharmaceutical, or a microbicide.

4. The method of claim 3 wherein the solvent further comprises a second pesticide.

5. The method of claim 3 wherein the solid further comprises a second pesticide.

6. The method of claim 3 further comprising after step b), step c) adding one or more pesticides to the suspension concentrate.

7. The method of claim 1 further comprising after step b): step c) milling the product of step b to reduce the size of the particles.

8. The method of claim 1 wherein the stream comprising melted solid further comprises a solvent.

9. The method of claim 1 further comprising after step b); step c) adding one or more formulation adjuvants to the suspension concentrate.

10. The suspension concentrate produced by the method of claim 1, 6, 7, or 9.

* * * * *